United States Patent [19]

Rittersdorf et al.

[11] Patent Number: 5,194,389
[45] Date of Patent: Mar. 16, 1993

[54] NAPHTHOL DERIVATIVES, PROCESSES FOR THEIR PRODUCTION AND THEIR USE

[75] Inventors: Walter Rittersdorf; Werner Guethlein, both of Mannheim; Peter Vogel, Hemsbach; Detlef Thym, Mannheim, all of Fed. Rep. of Germany

[73] Assignee: Boehringer Mannheim GmbH, Mannheim, Fed. Rep. of Germany

[21] Appl. No.: 698,447

[22] Filed: May 10, 1991

[30] Foreign Application Priority Data

May 15, 1990 [DE] Fed. Rep. of Germany ....... 4015591

[51] Int. Cl.$^5$ .............................................. G01N 33/20
[52] U.S. Cl. ........................................................ 436/79
[58] Field of Search ........................................... 436/79

[56] References Cited

U.S. PATENT DOCUMENTS

| 4,046,752 | 9/1977 | Hohmann et al. | 260/158 |
| 4,301,068 | 11/1981 | Giles et al. | 260/152 |

FOREIGN PATENT DOCUMENTS

| 041175 | 12/1981 | European Pat. Off. |
| 085320 | 8/1983 | European Pat. Off. |
| 125555 | 11/1984 | European Pat. Off. |
| 128317 | 12/1984 | European Pat. Off. |
| 128318 | 12/1984 | European Pat. Off. |
| 141647 | 5/1985 | European Pat. Off. |
| 1054740 | 4/1959 | Fed. Rep. of Germany |
| 2277832 | 2/1976 | France |
| 461679 | 10/1968 | Switzerland |

OTHER PUBLICATIONS

C.A.—9 3:151669W, (1980).
Hyman, Edward S., Biophys. Soc., Abstracts, 72a, WPM-J14.
K. Ueno and Mitakagi, (Jul. 1982), Studies in Phys. & Theor. Chem., 27:279-293.
Nakamura, Hiroshi et al., Bunseki Kagaku, 31:E131--E134, 1982.
S. Imura et al., Bunseki Kagaku, (1971), 20(6):704-708 (English translation).
Chem. Abst. 75:157991v, 1971.

Primary Examiner—John W. Rollins
Attorney, Agent, or Firm—Felfe & Lynch

[57] ABSTRACT

The subject matter of the present invention are naphthol derivatives having the general formula I

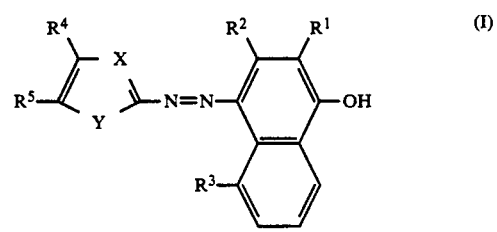

in which
$R^1$, $R^2$, $R^3$ are the same or different and each represents hydrogen, an alkyl or alkoxy group, in which at least one of the residues is a ($C_8$–$C_{30}$)-alkyl or alkoxy residue
$R^4$ is hydrogen or an alkyl group
$R^5$ is a nitro group, an alkyl group substituted by halogen, a cyano group, a sulfonamide group or an alkylsulfonyl group
X is nitrogen or the residue $CR^6$ and
Y is sulphur or the residue $CR^7 = CR^8$ in which $R^6$, $R^7$, $R^8$ are the same or different and each denotes hydrogen, halogen, a nitro group, a cyano group, an alkyl or an alkyl group substituted by halogen or an alkylsulfonyl group, a process for their production and their use as a pH indicator or in methods and agents for the determination of an ion in an aqueous liquid.

26 Claims, 1 Drawing Sheet

NAPHTHOL DERIVATIVES, PROCESSES FOR THEIR PRODUCTION AND THEIR USE

SUMMARY OF THE INVENTION

The invention concerns Naphthol derivatives which can be used as pH indicators or for determining an ion in an aqueous solution.

DESCRIPTION

Figure 1:
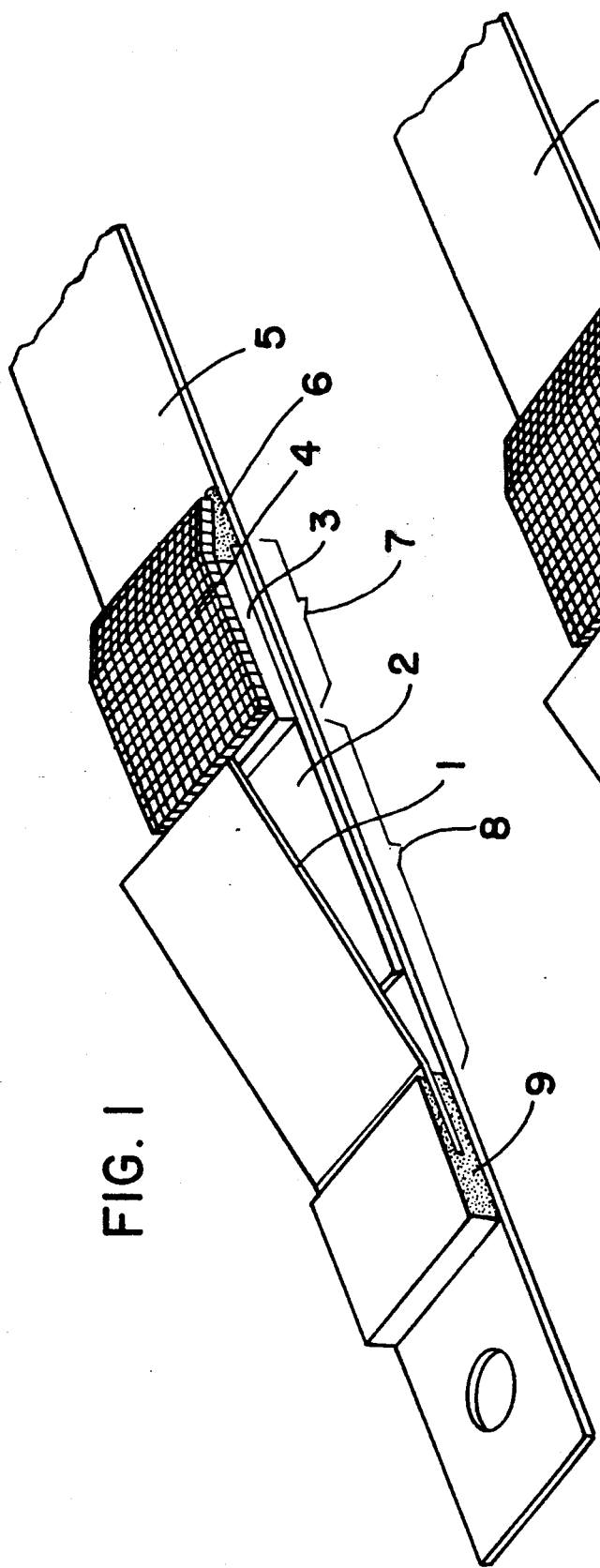
FIG. 1 describes a test strip.

The present invention concerns novel naphthol derivatives, a process for their production and their use as pH indicators. In addition the invention concerns a method for the determination of an ion in an aqueous liquid in which the ion passes into a phase which is immiscible with the aqueous liquid and as a result a pH indicator which is present there undergoes a colour change which is used for the determination of the ion.

In addition the invention concerns an agent for the determination of an ion in an aqueous liquid which contains an ionophore and a pH indicator.

Finally the invention concerns the use of a naphthol derivative for the production of an agent for the determination of an ion.

A multitude of methods are known for the determination of ions in solutions, in particular alkaline and alkaline-earth ions. Flame photometry, atomic absorption spectrometry and recently also ion-selective electrodes have gained most importance in this connection. All these methods require a considerable degree of instrumentation. For this reason one has tried to look for alternatives which enable the user to determine the ions with methods which are more simple to handle. Such methods are of interest inter alia for the rapid determination of sodium ions in sea water desalination or for the rapid determination of calcium ions in water softening. Methods which can be carried out rapidly and are simple to handle are particularly important in the determination of ions, in particular alkaline ions such as sodium and potassium ions, in body fluids such as blood, plasma, serum or urine inter alia in the laboratory diagnosis and emergency diagnosis of diseases of the cardiovascular system, muscle diseases, kidney diseases or states of shock of various causes. Lithium determinations are for example necessary in the monitoring of antidepressant therapies.

A multitude of methods which are based on liquid-liquid extraction of coloured anions are known for the simple determination of ions, such as alkaline ions, which are particularly important for the aforementioned diagnostic problems. In these methods an anionic dye is added to an aqueous solution of the cation and subsequently it is extracted by shaking with a solvent which contains an ionophore and is immiscible with water. The ionophore which is a complexing agent for the cations to be determined, such as alkaline ions, pulls together with the cation an amount of dye (which is proportional to the amount of cations present) into the liquid phase which is immiscible with water. After removing the aqueous phase (with the excess dye), the organic phase is then analysed visually or photometrically.

Although this method is widely used in wet chemistry it is of little use for the so-called dry chemistry. This term is understood to include test carriers, also named rapid diagnostics, in which all of the reagents which are required for the test reaction are present in a dry state in or on one or several carrier matrices such as absorptive materials or materials which are capable of swelling. For the quantitative determination of a substance, a liquid sample is applied to the test carrier and there it is brought into contact with the reagents which are necessary for the test reaction. A signal is formed as a measure of the substance to be determined, and this signal can be measured. If the signal is the formation of colour or change in colour, this can be evaluated visually or photometrically, preferably by reflectance photometry.

The simplicity of the test carrier principle contrasts with the difficulty of having to add a dye to the sample for the determination of an ion and then to have to remove its surplus. It is therefore not surprising that such a method disclosed in EP-A-0 041 175 has not become of importance for a dry test.

Methods of determining cations which are based on the principle of a so-called "heterogeneous pH reaction", as presented below, are more suitable for test carriers.

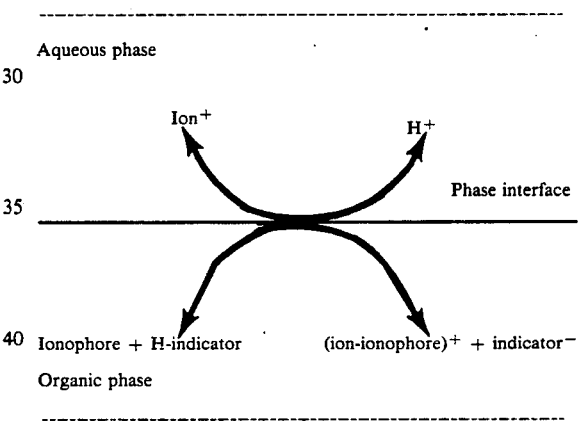

Aqueous phase

Ion$^+$  H$^+$

Phase interface

Ionophore + H-indicator   (ion-ionophore)$^+$ + indicator$^-$

Organic phase

In this case a two-phase system with an aqueous and an organic phase is present. A specific ionophore for the cation to be determined and a pH indicator are dissolved in the organic phase. Both chemical species can also be present as a chromoionophore, i.e. combined via a chemical bond to form a single molecule. The ion to be detected is taken up by the ionophore at the interface of the two phases, transported into the organic phase and then is present there as an ion-ionophore complex. In order to counterbalance the charge this causes the pH indicator, which is also present in the organic phase, to release a proton which is transferred into the aqueous phase. In this way an amount of coloured indicator anion is formed which is proportional to the concentration which was originally present in the aqueous phase of the ion to be detected.

This principle was first mentioned for liquid-liquid extractions in E. S. Hyman, Biophysical Society Abstracts, 1971, 72a and uses valinomycin as the ionophore and tetrabromophenolphthalein ethyl ester as the pH indicator.

Tetrabromophenolphthalein ethyl ester is also described as a pH indicator in EP-A-0 125 555 in a test carrier for the determination of ions.

The compound is not very stable since it is sensitive to hydrolysis. The tetrabromophenolphthalein which forms on hydrolysis is ineffective as a pH indicator for the purpose described herein, leading to interference with the test reaction.

Indonaphthol derivatives with alkyl side chains of different lengths are in particular described in Ep-A-0 128 317 and Ep-A-0 128 318 for test carriers for the determination of ions. Indonaphthols are not very amenable to synthesis if they are substituted by longer chains which is necessary to achieve the necessary lipophilicity for an adequate solubility in the organic phase and are thus expensive.

Chromoionophores are described for liquid-liquid extractions by K. Ueno et al., Studies in Physical and Theoretical Chemistry 27, 279-293 (1982) as well as by H. Nakamura, Bunseki Kagaku 31, E 131-E 134 (1982). Chromoionophores are mentioned for test carriers for the determination of ions in EP-A-0 085 320 and EP-A-0 141 647. This class of compounds is also difficult to prepare and thus expensive. In addition when designing a test one is very limited by the given ratio of chromophore to ionophore.

According to the present invention the disadvantages of the state of the art are eliminated by use of novel substances.

The substances should be easy to obtain i.e. low-priced and relatively simple to synthesize and should have the same chemical parent substance so that they are easy to vary in order to have the optimal pH indicator for each of the different applications, thus permitting sensitive measurements.

In addition, the novel substances should have an indicator transition point in non-aqueous media which allows aqueous samples with a pH between 5 and 10 to be examined for ions according to the principle of the heterogeneous pH reaction.

This object is achieved by the invention characterized in the patent claims.

The invention provides naphthol derivatives having the general formula I

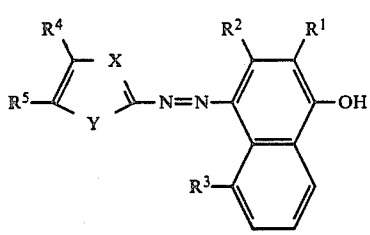

in which
  $R^1$, $R^2$, $R^3$ are the same or different and each represents hydrogen, an alkyl or alkoxy group in which at least one of the residues is a ($C_8$–$C_{30}$)-alkyl or alkoxy residue
  $R^4$ is hydrogen or an alkyl group
  $R^5$ is a nitro group, an alkyl group substituted by halogen, a cyano group, a sulfonamide group or an alkylsulfonyl group
  X is nitrogen
  Y is sulphur or the residue $CR^7=CR^8$
in which $R^6$, $R^7$, $R^8$ are the same or different and each denotes hydrogen, halogen, a nitro group, a cyano group, an alkyl or an alkyl group substituted by halogen or an alkylsulfonyl group.

The invention also provides a process for the production of a naphthol derivative as characterized above. The process is characterized in that
  a) a naphthoquinone having the general formula II

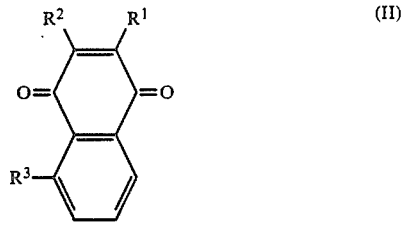

in which
  $R^1$, $R^2$, $R^3$ are the same or different and each represents hydrogen, an alkyl or alkoxy group, in which at least one of the residues is a ($C_8$–$C_{30}$)-alkyl or alkoxy residue
is reacted with a hydrazine having the general formula III

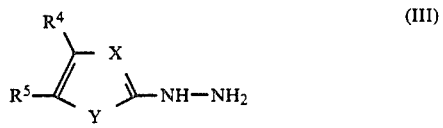

in which
  $R^4$ denotes hydrogen or an alkyl group
  $R^5$ denotes a nitro group, an alkyl group substituted by halogen, a cyano group, a sulfonamide group or an alkylsulfonyl group
  X denotes nitrogen or the residue $CR^6$ and
  Y denotes sulphur or the residue $CR^7=CR^8$
in which $R^6$, $R^7$, $R^8$ are the same or different and each denotes hydrogen, halogen, a nitro group, a cyano group, an alkyl group or an alkyl group substituted by halogen or an alkylsulfonyl group, or
  b) an amine having the general formula IV

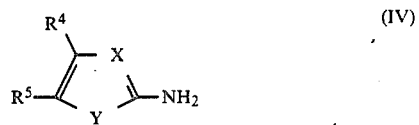

in which
  $R^4$, $R^5$, X and Y have the aforementioned meaning stated under a)
is converted into the corresponding diazonium salt and reacted in an azo coupling reaction with a naphthol having the general formula V

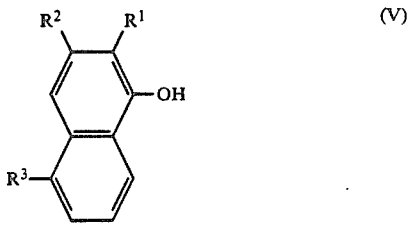

in which
  $R^1$, $R^2$ and $R^3$ have the aforementioned meaning stated under a).

Furthermore a subject matter of the present invention is the use of a naphthol derivative as characterized above as a pH indicator.

In addition the invention provides a method for the determination of an ion in an aqueous liquid in which the ion passes into a phase which is immiscible with the aqueous liquid and as a result a pH indicator which is present there undergoes a colour change which is used for the determination of the ion which is characterized in that a naphthol derivative of the aforementioned type is used as pH indicator.

Finally the invention provides an agent for the determination of an ion in an aqueous liquid containing an ionophore and a pH indicator in a water-immiscible medium which is characterized in that the pH indicator is a naphthol derivative as characterized above.

One aspect of the invention is the use of a naphthol derivative as characterized above for the production of an agent for the determination of an ion.

It was found that compounds having the general formula I are pH indicators within the meaning stated above which achieve the desired purpose.

An alkyl group in the definition of the residues $R^1$, $R^2$, $R^3$, $R^4$, $R^6$, $R^7$ and $R^8$ is understood as an alkyl residue with 1 to 30 carbon atoms. It is preferred that in particular the residues $R^4$, $R^6$, $R^7$ and $R^8$ are alkyl residues with 1 to 4 carbon atoms, in particular 1 to 2 carbon atoms. As to the residues $R^1$, $R^2$ and $R^3$, only one of the residues is preferably an alkyl residue with 8 to 30, preferably 10 to 20 carbon atoms. If the other residues in this group are alkyls, then it is preferred that they have 1 to 4, preferably 1 to 2 carbon atoms. Alkyl residues with more than 2 carbon atoms can be straight-chained or branched. In addition, the alkyl residue can also be partially unsaturated.

An alkyl group substituted by halogen in the definition of $R^5$, $R^6$, $R^7$ and $R^8$ is understood as an alkyl residue with 1 to 4 carbon atoms substituted by fluorine, chlorine, bromine or iodine. Alkyl residues with 1 to 2 carbon atoms substituted by fluorine are preferred. The trifluoromethyl residue is particularly preferred.

An alkoxy group in the definition of the residues $R^1$, $R^2$, $R^3$ is an alkoxy residue with 8 to 30, preferably 10 to 20 carbon atoms. The alkoxy residue can be straight-chained or branched, saturated or partially unsaturated.

Halogen in the definition of the residues $R^6$, $R^7$, $R^8$ can denote fluorine, chlorine, bromine or iodine; chlorine and bromine are preferred.

An alkylsulfonyl group in the definition of the residues $R^5$, $R^6$, $R^7$, $R^8$ denotes the group alkyl—$SO_2$—. In this connection the alkyl group represents an alkyl residue of 1 to 4, preferably 1 to 2 carbon atoms. The methylsulfonyl group is particularly preferred.

A sulfonamide group in the definition of the residue $R^5$ is understood as an unsubstituted amide (—$SO_2NH_2$) or an amide of a primary or secondary amine (—$SO_2NHR$ or —$SO_2NR_2$) Alkyl, aryl or aralkyl residues can be used as (R). In the case of the amide of a secondary amine, the substituents (R) can be the same or different. An alkyl residue in this connection is understood as a residue with 1 to 4 carbon atoms. An aryl residue denotes an aromatic residue with 6 to 10 carbon atoms. Preferred aryl residues are phenyl or naphthyl residues. Aralkyl residues are those residues in which the aryl moiety is an aromatic residue with 6 to 10 carbon atoms and the alkyl moiety is a residue with 1 to 4 carbon atoms. The benzyl residue is a preferred aralkyl residue. The unsubstituted sulfonamide group (—$SO_2NH_2$) is particularly preferred for the present invention.

Particularly preferred naphthol derivatives within the scope of the present invention are those in which one of the members $R^1$, $R^2$ and $R^3$ represents an alkyl or alkoxy residue with 8 to 30, preferably 10 to 20 carbon atoms and the other members of the aforementioned group denote hydrogen or an alkyl residue with 1 to 4, preferably 1 to 2 carbon atoms.

Particularly preferred naphthol derivatives are those in which $R^1$ represents an alkoxy group with 10 to 20 carbon atoms and $R^2$ and $R^3$ represent hydrogen and the other residues have the meaning stated for formula I.

The compounds having the general formula I are novel. They can be produced analogously to known processes. Several variants of the process are possible for the production of naphthol derivatives having the general formula I. First, naphthoquinones having the general formula II

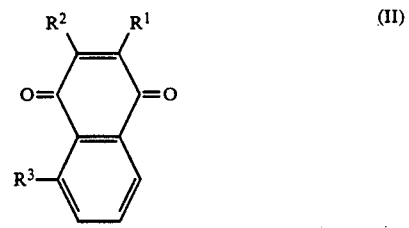

in which
$R^1$, $R^2$ and $R^3$ have the meaning stated for the general formula I are reacted with a hydrazine having the general formula III

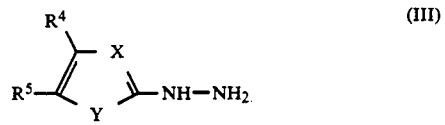

in which $R^4$, $R^5$, X and Y have the meaning stated for the general formula I. This reaction can take place under the usual conditions for the formation of a hydrazone.

The reaction preferably takes place under acidic conditions. The hydrazone per se is unstable and rearranges to form the desired naphthol having the general formula I.

Another method for the production of the naphthol derivatives according to the present invention having the general formula I starts with amines having the general formula IV

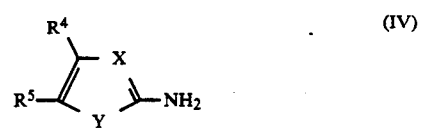

in which $R^4$, $R^5$, X and Y have the meanings stated for the formula I. These amines are diazotized and the resulting diazonium salts are reacted in an azo coupling reaction with a naphthol having the general formula (V)

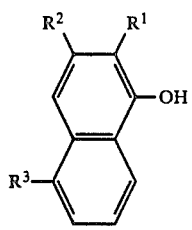

(V)

in which $R^1$, $R^2$ and $R^3$ have the meaning stated for the general formula I.

The diazotization of the amines having the general formula IV can take place in the usual manner. It has proven to be advantageous to prepare concentrated mineral acids, for example concentrated sulphuric acid with a nitrite, preferably sodium nitrite and then to add the amine having the general formula IV while cooling to room temperature. A diazotization mixture which also contains glacial acetic acid apart from sodium nitrite and concentrated sulphuric acid has proven to be especially advantageous. The preferred volume ratio of sulphuric acid and glacial acetic acid is between 1:1 and 2:1. The ratio of nitrite and the amine to be diazotized having the general formula IV is usually equimolar.

After completion of the diazotization reaction the reaction mixture is processed in aqueous solutions. For this purpose the reaction mixture is preferably poured into iced water. The diazonium salt per se is not isolated but is made to azo-couple with the naphthol having the general formula V in the aqueous processing solution. This is preferably carried out under weakly acidic conditions. Naphthols having the general formula V are only very sparingly soluble in aqueous solutions. They are therefore applied in organic solvents. Chloroform is for example well suited as the organic solvent. In this way a diazonium salt solution which is present after the aqueous processing can be added to a solution of a naphthol having the general formula V in chloroform and glacial acetic acid, and an acetate can be added to buffer the pH value of the reaction medium. In most cases the naphthol derivatives which form having the general formula I precipitate out of the reaction mixture. The product can then be re-crystallized or purified chromatographically.

The naphthol derivatives having the general formula according to the present invention are very well suited for indicating changes in the hydrogen ion concentration in a solution by a change in colour. The compounds are only sparingly soluble in aqueous solutions but are all the more soluble in organic solvents. They are resistant to hydrolysis and insensitive to substances which act reductively such as for example ascorbic acid. The substances according to the present invention can be handled without difficulty and are so stable, in particular in final test compositions, that they can be readily stored therein.

In addition the pH indicators allow very sensitive measurements since they have a very large shift in wavelength i.e. a shift in the wavelength of the maximum absorbance. Because of their properties they are very well suited to an application in methods for the determination of an ion in an aqueous liquid, in particular those based on the principle of the "heterogeneous pH reaction" as described at the beginning. In this respect the naphthol derivatives according to the present invention having the general formula I can be used in liquid-liquid extractions as described in principle by E. S. Hyman, Biophysical Society Abstracts, 1971, 72a as well as on "dry chemistry" test carriers which operate according to the principle of the heterogeneous pH reaction. Methods for the determination of an ion in an aqueous liquid which proceed according to the principle of the heterogeneous pH reaction have in common that the ion to be determined passes from the aqueous sample liquid into a phase which is immiscible with the aqueous liquid and as a result a pH indicator which is present there undergoes a change in colour which is used for the determination of the ion. Naphthol derivatives having the general formula I, in particular those compounds which were mentioned there as being particularly preferred, are very well suited for such methods.

An agent according to the present invention for the determination of an ion in an aqueous liquid contains in an organic medium which is immiscible with water an ionophore which is responsible for transporting the ion to be determined from the aqueous liquid into the organic phase in addition to the pH indicator soluble in an organic medium. In this connection "dry chemistry" test carriers for the determination of ions will be elucidated in more detail in the following. However, it is self evident to one skilled in the art that in principle the following statements apply basically in an analogous manner to liquid-liquid extractions and thus to non-test-carrier-bound test procedures.

Test carriers for the determination of ions which are based on the principle of the heterogeneous pH reaction are known from the state of the art as described in the introduction. They differ mainly in the way in which the organic phase is produced in a form which is appropriate for test carriers. In general the organic phase consists of relatively non-volatile organic liquids which are immiscible with water and/or hydrophobic polymers. If both are present together then they are referred to as plasticized plastics.

The naphthol derivatives according to the present invention having the general formula I can, in principle, be used in all of the test carriers for the determination of ions known from the state of the art which are based on the principle of the heterogeneous pH reaction. They have, however, proven to be particularly advantageous in test carriers in which they are present in a film layer which contains a film resistant to liquids consisting of a hydrophobic polymer and inert solid particles dispersed therein. Such test carriers are described in DE-A-40 15 590.0. Examples of such test carriers are shown in FIGS. 1 and 2.

Figure 2:
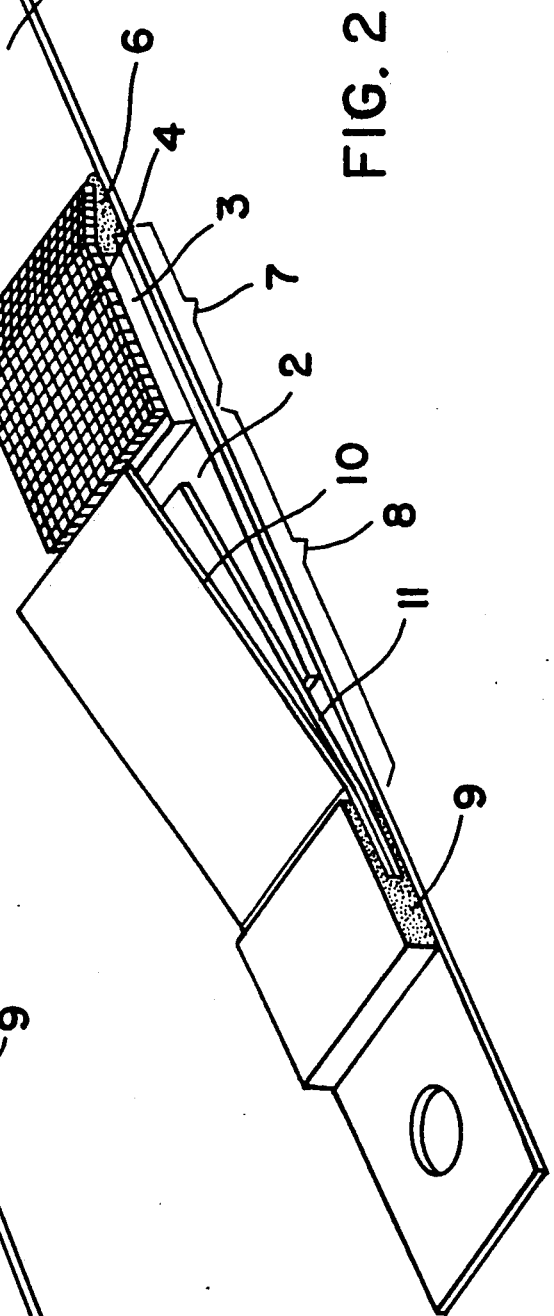
FIG. 2 describes a test strip differing from that in FIG. 1.

Two test carriers which are suitable for the determination of ions in blood are shown spatially in FIGS. 1 and 2. They allow the serum or plasma to be isolated from whole blood and the determination of the ions of interest in the liquid obtained in this way. The test carriers differ mainly in the location of the buffer substance within the test carrier. Details of the composition of the devices are as follows:

FIG. 1: A transport layer (2) which serves to transport the sample liquid from the sample application zone (7) into the test zone (8) is fixed onto an inert carrier foil (5) for example a plastic foil. In principle all materials which are able to transport the liquid to be examined from the sample application zone (7) into the test zone (8) and which in this process do not alter it in such a way that the analysis becomes impaired are suitable as the transport layer (2). It is particularly preferable to use a glass fibre fleece as the transport layer (2). A layer (3) for the separation of corpuscular components from the sample liquid is attached to the transport layer (2) and partially covers it. Basically any material can be used for this which enables corpuscular components from the sample liquid, in particular blood cells, and above all erythrocytes from blood, to be separated off and does not allow them to reach the test zone (8) in substantial amounts in order that they do not cause an interference in the test reaction there. In addition the separating layer (3) should not lead to a change in the sample liquid such that the concentration therein of the ions to be determined is changed and thus the result is falsified. Glass fibre fleeces, such as those described e.g. in EP-B-0 045 476, have proven to be particularly suitable for the separating layer (3). A protective layer (4) is mounted over the separating layer (3) which is intended to prevent damage of the separating layer (3) during the sample application, for example with a pipette. A net of inert material, for example of plastic, has proven to be of value for this. The protective layer (4) and separating layer (3) are fixed onto the inert carrier foil This can for example be carried out by means of a of hot-melting adhesive (6). A carrier foil consisting of transparent plastic with a film layer (1) which contains the reagents necessary for carrying out the determination (also including a naphthol derivative according to the present invention as a pH indicator) is attached to one side of the transport layer (2). This is preferably effected by a glued joint (9) for example a strip of hot-melting adhesive. The film layer (1) is positioned so that it can be brought into contact with the transport layer (2) in such a way that liquid transfer is possible by pressing the transparent carrier foil in the direction of the inert carrier foil (5).

The film layer (1) contains a film which is resistant to liquids and of a hydrophobic polymer and particles dispersed therein. The hydrophobic polymer is impermeable to the liquid to be examined and it is also impermeable to the ions to be determined. The particles enable the sample liquid to penetrate into the film layer. The film layer (1) as such is impermeable to the liquid to be examined. A certain volume is merely taken up. Hydrophobic polymers which have proven to be advantageous are in particular copolymers of vinyl acetate. Particularly advantageous are copolymers of vinyl acetate with vinyl laurate or maleic acid dibutylester.

Solid, inert, inorganic or organic particles which are insoluble in the liquids to be examined and which have an oil absorption value of 80–200, preferably 100–170 can be used as the particles. In particular the different types of diatomaceous earths such as unbaked or natural kieselguhr, calcinated or baked kieselguhr, flow baked or activated kieselguhr have proven to be particularly advantageous for the film layer (1).

The oil absorption value is a well known parameter in the field of paints and coatings for particles which are for example used as fillers. It is a measure for the interaction between the particles and the medium in which they are dispersed. The oil absorption value is simple to determine. The determination is carried out according to DIN (German Industrial Standard) 53199. According to this norm the oil absorption value indicates the amount of linseed oil in g which is needed in order to process 100 g of the particles of interest into a coherent putty-like mass.

As a rule the particles used have a non-uniform shape. Their particle size is usually between 0.1 and 200 $\mu$m, preferably between 0.2 and 30 $\mu$m. A particular feature of the particles used according to the present invention is that they have cavities into which gases and wetting liquids can penetrate. An expression of this property is in particular the low bulk density of 50 to 250, preferably 80 to 180 g/l.

A ratio by weight of hydrophobic polymer to particle of 5:1 to 1:10 is useful for the film layer (1). The ratio by weight is preferably 1:1 to 1:3. The optimal ratio by weight of hydrophobic polymer to particle is in any case dependent on the nature of the polymer used and the particles. If the hydrophobic polymer is a copolymer of vinyl acetate with vinyl laurate or maleic acid dibutylester and the particles are diatomaceous earths, the optimal ratio by weight is between 1:1.5 and 1:2.5.

Further necessary constituents of the film layer (1) are a difficultly volatile liquid which is immiscible with water, an ionophore and a naphthol derivative according to the present invention. These components are distributed homogeneously in the hydrophobic polymers.

A difficultly volatile liquid which is immiscible with water is understood as a plasticizer for plastics. It serves, together with the polymer as the actual organic phase for the method of determination of the ions according to the principle of the heterogeneous pH reaction. All possible commercial types of plasticizer, preferably sebacic acid., acrylic acid, phthalic acid and phosphoric acid-esters as well as silicons come into consideration as the plasticizer. In particular for technical reasons concerning the processing, the very difficultly volatile Uvinul ® N539 (2,2-diphenyl-1-cyanoacrylic acid ethylhexylester) is preferred.

The ratio by weight of hydrophobic polymer to difficultly volatile, hydrophobic, organic liquid in the test layer can be between about 5:1 to about 1:5, in particular between about 2:1 to about 1:2.

All substances which can complex the ions can be used as the ionophore which are specific for the ions to be determined and sufficiently soluble in a non-aqueous phase. In this connection crown ethers, cryptands, podands and corresponding peptides of a cyclic or acyclic nature come into consideration. 2,3-naphtho-15-crown-5 has proven to be particularly advantageous for the determination of potassium. The natural ionophore valinomycin is especially preferred. For the determination of sodium N,N'-dibenzyl-N'N-diphenyl-1,2-phenylene-dioxydiacetamide comes for example into consideration, for lithium N,N'-diheptyl-5,5-dimethyl-N,N'-di(3-oxapentyl)-3,7-dioxanonane-diamide and for calcium diethyl-N,N'-[(4R,5R)-4,5-dimethyl-1,8-dioxo-3,6-dioxa-octamethylene]-bis-(12-methylaminododecanoate).

Since naphthol derivatives according to the present invention are used as pH indicators and since they are sensitive to changes in pH, it is particularly advantageous to also incorporate a buffer in the film layer (1). In determination methods for ions which are based heterogeneous pH reaction, the pH of a buffer controls the transfer of the proton from the non-aqueous into the aqueous phase. In diagnostic agents for the determination of ions in body fluids the buffer substance is preferably chosen so that the pH can be adjusted to a value between 5–10, preferably between 7 to 8. In principle all the usual buffers come into consideration for this, provided they are soluble in water and do not contain ions which interfere with the test reaction. Buffers have proven to be suitable which are from the so-called Good buffer series such as e.g. N,N-bis-(hydroxyethyl)-aminoethanesulfonic acid (BES), 3-[N-trishydroxymethyl]-methylamino-hydroxypropanesulfonic acid (TAPSO) or N-hydroxyethylpiperazine-N-propanesulfonic acid (HEPPS).

If ionophores are used which are not sufficiently selective for the ion to be determined then water soluble complexing agents can be added which mask the interfering ions. Thus, for example a possible interference of a sodium test by calcium is prevented with ethylenediaminetetraacetate (EDTA).

In addition wetting agents can be used to improve the production of the films or the wetting of the films by the sample to be examined. Only those agents can be used for this which do not interfere with the test reaction. These are in particular non-ionic and zwitterionic compounds. Of the non-ionic wetting agents polyethylene glycol ethers or esters, preferably Triton ® X100 have for example proven to be advantageous. n-decyl-N,N-dimethyl-3-ammonio-1-propanesulfonate (Zwittergent ® 3-10) can be used advantageously as a zwitterionic wetting agent.

In order to improve the consistency of the film layer (1), thickeners can be used in addition. Ethylcellulose has proven to be particularly advantageous for this. In addition to this hydrophilic thickening agents, such as for example hydroxyethyl- or hydroxypropylcellulose, can also be added to the film layer (1) for the aqueous phase which is present after wetting the film layer (1) with an aqueous liquid to be analyzed.

In order to produce a film layer (1), all components which, when the film layer is used for the determination of an ion in an aqueous liquid, in particular in a body fluid such as blood, plasma, serum or urine, should not be taken up in the aqueous phase but rather should remain in the organic phase i.e. the film layer (hydrophobic polymer; difficultly volatile liquid which is immiscible with water; ionophore; naphthol derivative according to the present invention; if desired, thickener for improving the consistency of the film layer) are dissolved in a highly volatile to moderately volatile organic solvent. The particles are stirred into this solution and dispersed homogeneously therein. Afterwards the paste is spread out on a support with a doctor blade and dried. Of course other suitable methods of application can also be used such as roll coating, film casting or similar procedures. The dry film layer has a thickness of 20 to 500, preferably of 20 to 150 μm.

There are different ways of incorporating components (buffer; if desired complexing agent; if desired wetting agent; if desired thickener for changing the consistency of the aqueous phase) which are taken up into the aqueous phase when the aqueous sample liquid is applied to the film layer (1). One possibility is to coat the particles with the aforementioned components by evaporating, spray drying or freeze drying the particles together with an aqueous solution of the components. The particles coated in this way are then stirred into the organic solvent as described above. Another possibility is to first produce the film layer with untreated particles, then to re-coat with an aqueous solution of the aforementioned components and finally to dry.

FIG. 2 differs from FIG. 1 in that a layer (11), which contains those substances which are taken up into the aqueous phase during the determination reaction, is mounted between the film layer (10) and transport layer (2) likewise via the glued joint (9) which is, for example a strip of hot-melting adhesive. Such substances are e.g. buffer substances. Complexing agents, wetting agents or thickeners for changing the consistency of the aqueous phase can be incorporated into the additional layer (11) of the test carrier according to FIG. 2 instead of in the film layer (1) of the test carrier according to FIG. 1 or (10) of the test carrier according to FIG. 2. Absorptive materials come into consideration as materials for the additional layer (11) which enable a liquid transfer to a further layer when this is brought into contact with it. Paper is particularly advantageous in this regard, but nets made of inert materials such as plastic can also be used.

In order to carry out the determination of an ion in blood by means of one of the test carriers shown in the figures, the sample is applied to the protective layer (4). The blood penetrates into the separation layer (3) and erythrocytes are separated from plasma or serum. The liquid obtained in this way is sucked into the test zone (8) by capillary forces. The aqueous phase in the transport layer (2) is brought into contact with the film layer by pressure on the carrier foil with the film layer (1) or (10), liquid penetrates into the film layer and the determination reaction is triggered. The colour formed in the film layer which is a result of the reaction is observed visually or measured by reflectance photometry through the carrier foil of the film layer (1) or (10).

The following Table 1 indicates the advantageous and preferred percentages by weight of the components of a film layer (1) or (10):

TABLE 1

| Component of the film layer | Content of the film layer in % by weight | |
|---|---|---|
| | advantageous | preferred |
| polymer | 5–60 | 20–40 |
| difficultly volatile liquid which is immiscible with water | 5–70 | 20–40 |
| particles | 15–80 | 30–50 |
| ionophore | 0.05–5.0 | 0.2–1.0 |
| naphthol derivative according to the invention | 0.05–5.0 | 0.2–0.7 |

If the buffer substance is applied in or onto the film layer (1) then this contains 5–30, preferably 10–20% by weight buffer. The substances which can be used, if desired, such as complexing agents, wetting agents or thickeners are in amounts—if they have been applied in or onto the film layer (1)—of 0.005 to 5, preferably 0.02 to 2% by weight of the film layer according to the present invention.

The invention is elucidated further in the following examples.

EXAMPLE 1 a) 2(3,7,11,15-tetramethyl-2-hexadecenyl)-3-methyl 4-[(2,4-dinitrophenyl) azo]-1-naphthol 19.8 g (0.1 mol) 2,4-dinitrophenylhydrazine is suspended in 400 ml ethanol with addition of 9 ml (0.11 mol) concentrated hydrochloric acid in a 2 l three-neck flask with stirrer, cooler and thermometer and 45 g (0.1 mol) vitamin $K_1$ [2-methyl-3-(3,7,11,15-tetramethyl-2-hexadecenyl)-1,4-naphthoquinone] are added, stirred for 15 minutes at room temperature, and then heated for 4 hours under reflux. Afterwards it is concentrated in a vacuum. 64 g of a red-brown, viscous mass are obtained. This is purified chromatographically on a silica gel 60 (Merck) column, inside diameter 10.5 cm, filling height 110 cm with methylene chloride/n-heptane=2:1 as mobile solvent. Because of the poor solubility of the reaction product, the crude product is dissolved in 350 ml of the mobile solvent, insoluble constituents are filtered off over a Seitz filter and it is applied to the silica gel column. The appropriate batches are combined, concentrated in a vacuum and the orange-coloured, wax-like product is re-crystallized twice from 100 ml each time of n-propanol/ligroin 1:1, the residue is washed twice with 20 ml n-propanol/ligroin 1:1 and dried until constancy of weight. One obtains 19.41 g (31% of the theoretical yield) orange-coloured, wax-like crystals which is uniform in TLC, mp 110° C. Transmission spectra at an acid or alkaline pH in o-nitrophenyloctyl ether yield $\lambda_{max}$ values of 440 or 616 nm.

The following can be produced in an analogous manner:

b) 2-(3,7,11,15-tetramethyl-2-hexadecenyl)-3-methyl-4-[(4-nitrophenyl)azo]-1-naphthol, TLC, silica gel 60 (Merck), mobile solvent: toluol/methanol=50:1; $R_f$=0.22, from 4-nitrophenylhydrazine, Transmission spectra at an acid or alkaline pH in o-nitrophenyloctyl ether yield $\lambda_{max}$ values of 455 or 637 nm.

c) 2-(3,7,11,15-tetramethyl-2-hexadecenyl)-3-methyl-4-[(2-methyl-4-nitrophenyl)azo]-1-naphthol, TLC, silica gel 60 (Merck), mobile solvent: methylene chloride/n-heptane=3:1, $R_f$=0.31 from 2-methyl-4-nitrophenylhydrazine, Transmission spectra at an acid or alkaline pH in o-nitrophenyloctyl ether yield $\lambda_{max}$ values of 447 or 642 nm.

d) 4-(2-methyl-2-hydroxy-3-[(3,7,11,15-tetramethyl-2-hexadecenyl) -1-naphthol)azo]-3-nitrobenzonitrile amorphous, TLC, silica gel 60 (Merck), mobile solvent: methylene chloride/n-heptane 2:1, $R_f$=0.21, from 2-hydrazino-5-nitrobenzonitrile (Parnell, Chem. Soc. 1959, 2363), Transmission spectra at an acid or alkaline pH in o-nitrophenyloctyl ether yield $\lambda_{max}$ values of 499 or 574 nm.

e) 2-(3,7,11,15-tetramethyl-2-hexadecenyl)-3-methyl-4-[(4-amino-sulfonyl-2-nitrophenyl)azo]-1-naphthol Fp 122° C., TLC, silica gel 60 (Merck), mobile solvent: toluol/methanol 5:1, $R_f$=0.38, from 4-amidosulfonyl-2-nitrophenylhydrazine which is produced as follows:

4.88 g (0.021 Mol) 4-amidosufonyl-2-nitrochlorobenzol (obtainable according to P. Fischer, Chem. Ber. 24, 3190 (1891)) are stirred with a solution of 5.25 ml (0.105 Mol) hydrazine hydrate in 150 ml methanol for half an hour at room temperature, the orange-red crystals which form are aspirated, the filter residue is washed with a small volume of methanol and after drying over diphosphorus pentoxide, 3.64 g (which corresponds to 75% of the theoretical yield) of the desired hydarzine derivative is obtained. Fp 217°-219° C. Transmission spectra at an acid or alkaline pH in o-nitrophenyloctyl ether yield $\lambda_{max}$ values of 450 or 566 nm.

f) 2-(3,7,11,15-tetramethyl-2-hexadecenyl)-3-methyl-4-[(2,4-di(methanesulfonyl)phenyl)azo]-1-naphthol amorphous, TLC, silica gel 60 (Merck), mobile solvent: toluol/ethyl acetate 5:1, $R_f$=0.23 from 2,4-di(methanesulfonyl)phenylhydrazine Transmission spectra at an acid or alkaline pH in o-nitrophenyloctyl ether yield $\lambda_{max}$ values of 462 or 562 nm.

g) 2-(3,7,11,15-tetramethyl-2-hexadecenyl)-3-methyl-4-[(2,4,6-trinitrophenyl)azo]-1-naphthol amorphous, TLC, silica gel 60 (Merck), mobile solvent: methylene chloride/n-heptane 2:1, $R_f$=0.55, from 2,4,6-trinitrophenylhydrazine. Transmission spectra at an acid or alkaline pH in o-nitrophenyloctyl ether yield $\lambda_{max}$ values of 495 or 600 nm.

h) 2-(3,7,11,15-tetramethyl-2-hexadecenyl)-3-methyl-4[(2,6-dinitro-4-cyanophenyl)azo]-1-naphthol amorphous, TLC, silica gel 60 (Merck), mobile solvent: methylene chloride, $R_f$=0.62, from 4-hydrazino-3,5-dinitrobenzonitrile (U.S. Pat. No. 3,935,183), Transmission spectra at an acid or alkaline pH in o-nitrophenyloctyl ether yield $\lambda_{max}$ values of 440 or 562 nm.

i) 2-(3,7,11,15-tetramethyl-2-hexadecenyl)-3-methyl-4-[(3,5-dinitro-2-thinyl)azo]-1-naphthol, amorphous, TLC, silica gel 60 (Merck), mobile solvent: toluol/methanol 5:1, $R_f$=0.28, from 2-hydrazino-3,5-dinitrothiophene (H. Beyer et al., J. Prakt. Chem. 296, 91 (1964).

j) 2-(3,7,11,15-tetramethyl-2-hexadecenyl)-3-methyl-4-[(5-nitro-2-thiazolyl)azo]-1-naphthol amorphous, TLC, silica gel 60 (Merck), mobile solvent: toluol/methanol 5:1, $R_f$=0.32, from 2-hydrazino-5-nitro-1,3-thiazole (DE-A-23 29 295,.

Transmission spectra at an acid or alkaline pH in o-nitrophenyloctyl ether yield $\lambda_{max}$ values of 450 or 652 nm.

EXAMPLE 2

4-[2,6-dibromo-4-nitrophenyl)azo]-2-octadecyloxy-1-naphthol a) 2-octadecyloxynaphthalene 172.8 g (1.2 mol) 2-naphthol (98%) is added to a solution of 48 g (1.2 mol) sodium hydroxide (99%) in 1 l ethanol in a 4 l three-neck flask with stirrer, cooler and thermometer, after it has dissolved 417 g (1.25 mol) n-octadecylbromide are added and the reaction mixture is heated for 14 hours under reflux. After addition of a further 1 l ethanol the hot solution is aspirated over a Seitz filter to remove inorganic material and the weak pink coloured filtrate is brought to crystallization by placing it in an ice bath for 30 minutes. After aspiration of the almost colourless crystals, the filter cake is washed in portions with ca 700 ml ethanol and after drying over diphosphorus pentoxide 371.9 g (93.7% of the theoretical yield) 2-octadecyloxynaphthalene are obtained as colourless crystals, mp 64°-68° C.

TLC: silica gel 60 (Merck), mobile solvent: n-heptane/methylethyl ketone 2:1, $R_f$=0.34.

b) 2-octadecyloxy-1-naphthol 594 g (1.5 mol) 2-octadecyloxynaphthalene and 397 g (0.75 mol) lead tetraacetate are added to a mixture of 3 l glacial acetic acid and 600 ml acetic anhydride in a 10 l three-neck flask with stirrer, Claisen attachment, thermometer and cooler with a calcium chloride tube and it is heated to 55° C. Over a period of 4 days a further 400 g lead tetraacetate are added in portions (each of 100 g) at intervals of 24 hours while stirring. Afterwards the yellow solution which is formed is cooled to room temperature, stirred again for 30 minutes after addition of 1.5 l water, the crystal slurry which forms is aspirated and washed in portions with 2 l water. The wet crude product is dissolved in 4 l toluol and shaken three times with 1 l portions of water, three times with 1 l saturated sodium hydrogen carbonate solution and then again three times with 1 l water. After drying the toluol phase over sodium sulphate, aspiration and concentration by evaporation, 635 g brown crude product are obtained which is purified chromatographically as follows: the crystallizate obtained is dissolved in a mixture of 1.3 l toluol/isohexane 5:2 and the solution is applied to a silica gel 60 (Merck) column, inside diameter 11.5 cm, filling height 1.2 m. Toluol/isohexane 5:2 is used as the mobile solvent and fractions of ca 300 ml are taken. Fractions 9–52 are combined and concentrated by evaporation until constancy of weight. One obtains 324.2 g 2-octadecyloxy-1-naphthol acetate, Fp 67°–68° C. This is dissolved without further purification in 1.8 l methanol while heating and cooled to 20° C. 93 ml concentrated sulphuric acid are added dropwise to the suspension which forms within 15 minutes without cooling and while stirring, whereby the temperature increases to 35° C. Subsequently it is heated for 2 hours under reflux, then cooled with an ice bath and stirred for a further 30 minutes while cooling on ice. The crystals which form are aspirated, washed with 150 ml ice-cold methanol and dried at 35° C. in a drying cupboard over diphosphorus pentoxide. One obtains 294.4 g (47.5% of the theoretical yield) 2-octadecyloxy-1-naphthol, colourless crystals, mp 58°–59° C.

c) 4-(2,6-dibromo-4-nitrophenyl)azo]-2-octadecyloxy-1-naphthol 22.7 g (0.33 mol) sodium nitrite are fed into 300 ml concentrated sulphuric acid in a 2 l three-neck flask with stirrer, Claisen attachment and thermometer during 10–15 minutes while stirring whereby the temperature of the reaction solution is allowed to increase to 35° C. It is then cooled to 20° C. and 230 ml glacial acetic acid are added dropwise in ca 15–20 minutes in such a way that the temperature is held at 20°–25° C. while cooling on ice. Afterwards 97.6 ml (0.33 mol) 2,6-dibromo-4-nitroaniline (Riedel de Haen [99%GC] are added in portions during 10 minutes while cooling occasionally whereby the temperature is kept at 19°–21° C. and it is stirred again for a further 3 hours. Afterwards it is poured onto 3.5 l iced water and the diazonium salt solution which forms is added rapidly to a solution of 124 g (0.3 mol) 2-octadecyloxy-1-naphthol in a mixture of 3 l glacial acetic acid and 300 ml chloroform with addition of 180 g (1.33 mol) sodium acetate-trihydrate. (In the production of the solution of the naphtholether care must be taken that after it has been fed into glacial acetic acid/chloroform with addition of sodium acetate it is again cooled down to 20° C. after a temperature increase to ca 45° C.) After stirring for 3 hours in the ice bath the crystallizate which is formed is aspirated, the residue is washed three times with 500 ml water each time and dried in a drying cupboard at 40° C. The crude product—295.5 g light brown crystals—is purified chromatographically. The azo compound is dissolved in 1 l toluol/methylene chloride 2:5 and applied to a silica gel 60 (Merck) column with an inside diameter of 11.5 cm, filling height of 1.2 m and eluted with toluol/methylene chloride 2:5. Fractions of ca 70 ml are taken. The fractions 57–173 are combined and concentrated by evaporation. One obtains 134.2 g brown crystals. These are dissolved in 480 ml toluol at 80° C., cooled to 65° C. and 800 ml isohexane are added while stirring vigorously. It is allowed to cool to 20° C. while stirring, placed overnight in a refrigerator, the crystals which form are aspirated and the filter cake is washed twice with 300 ml ice-cold toluol/isohexane 1:1.3 and subsequently with 300 ml isohexane. Afterwards it is dried in a drying cupboard at 40° C. over diphosphorus pentoxide until constancy of weight. One obtains 119.9 g (55.5% of the theoretical yield) azo compound, light brown crystals, Fp 102°–103° C. TLC, silica gel 60 (Merck), mobile solvent: toluol/methylene chloride 2:5, $R_f$=0.38, Transmission spectra at an acid or alkaline pH in o-nitrophenyloctylether yield $_{max}$ values of 454 or 672 nm.

EXAMPLE 3

The following substances can be produced analogous to Example 2:

a) 4-[(2-nitro-4-trifluoromethylphenyl)azo]-2-octadecyloxy-1-naphthol, mp 95°–97° C., from 2-nitro-4-trifluoromethylaniline Transmission spectra at an acid or alkaline pH in o-nitrophenyloctyl ether yield $\lambda_{max}$ values of 470 or 604 nm.

b) 4-[(4-nitro-2-trifluoromethylphenyl)azo]-2-octadecyloxy-1-naphthol, mp 135°–138° C., from 4-nitro-2-trifluoromethylaniline; Transmission spectra at an acid or alkaline pH in o-nitrophenyloctyl ether yield $\lambda_{max}$ values of 456 or 664 nm.

c) 4-[(2,4-dinitrophenyl)azo]-2-octadecyloxy-1-naphthol, mp 177°–178° C., from 2,4-dinitroaniline Transmission spectra at an acid or alkaline pH in o-nitrophenyloctyl ether yield $\lambda_{max}$ values of 456 or 632 nm.

d) 4-[(2-methanesulfonyl-4-nitrophenyl)azo]-2-octadecyloxy-1-naphthol, mp 117° C., from 2-methanesulfonyl-4-nitroaniline.

e) 4-[(4-ethanesulfonyl-2-nitrophenyl)azo]-2-octadecyloxy-1-naphthol, mp 165° C. from 4-ethanesulfonyl-2-nitroaniline, f) 2-[(4-hydroxy-2-octadecyloxy-1-naphthyl)azo-5-nitrobenzonitrile, mp 147°–149° C. from 2-cyano-4-nitroaniline g) 4-[2,6-dichloro-4-methanesulfonylphenyl)azo]-2-octadecyloxy-1-naphthol, mp 95° C. from 2,6-dichloro-4-methanesulfonylaniline (EP-A-0 039 312)

h) 4-[2-bromo-6-chloro-4-nitrophenyl)azo]-2-octadecyloxy-1-naphthol, mp 94°–96° C. from 2-bromo-6-chloro-4-nitroaniline i) 4-[(2-chloro-4,6-dinitrophenyl)azo]-2-octadecyloxy-1-naphthol, mp 99°–102° C. from 2-chloro-4,6-dinitroaniline Transmission spectra at an acid or alkaline pH in o-nitrophenyloctyl ether yield $\lambda_{max}$ values of 447 or 645 nm.

j) 2-[(4-hydroxy-2-octadecyloxy-1-naphthyl)azo]-3-bromo-5-nitrobenzonitrile, mp 178°–189° C. from 2-bromo-6-cyano-4-nitroaniline (U.S. Pat. No. 2,300,447)

k) 4-[2,4,6-trinitrophenyl)azo]-2-octadecyloxy-1-naphthol, TLC, silica gel 60 (Merck). Mobile solvent: n-heptane/methylketone 4:3, $R_f$=0.24 from 2,4,6-trinitroaniline Transmission spectra at an acid or alkaline pH in o-nitrophenyloctyl ether yield $\lambda_{max}$ values of 452 or 594 nm.

l) 2-[(4-hydroxy-2-octadecyloxy-1-napthyl)azo]-3,5-dinitrobenzonitrile, mp 122°–123° C. from 2-cyano-4,6-dinitroaniline, Transmission spectra at an acid or alkaline pH in o-nitrophenyloctyl ether yield $\lambda_{max}$ values of 448 or 602 nm.

m) 2-[(4-hydroxy-2-octadecyloxy-1-naphthyl)azo]-5-nitro-1,3-benzodinitrile, mp 160°–163° C. from 2,6-dicyano-4-nitroaniline (DE-A-2137719) Transmission spectra at an acid or alkaline pH in o-nitrophenyloctyl ether yield $\lambda_{max}$ values of 502 or 609 nm.

n) 4-[(2,6-dibromo-4-methanesulfonylphenyl)azo]-2-octadecyloxy-1-naphthol, mp 99°–102° C. from 2,6-dibromo-4-methanesulfonylaniline (EP-A-0 039 312), Transmission spectra at an acid or alkaline pH in o-nitrophenyloctyl ether yield $\lambda_{max}$ values of 442 or 608 nm.

o) 4-[(2-bromo-6-methanesulfonyl-4-nitrophenyl)azo]-2-octadecyloxy-1-naphthol, mp 210° C. from 2- bromo-6-methanesulfonyl-4-nitroaniline (DE-A-2516032).

p) 4-[(2-bromo-4-nitro-6-trifluoromethylphenyl)azo]-2-octadecyloxy-1-napthol, mp 84° C., from 2-bromo-4-nitro-6-trifluoromethylaniline, (M. Hauptschein et al., J. Amer. Chem. Soc. 76, 1051 (1954), Transmission spectra at an acid or alkaline pH in o-nitrophenyloctyl ether yield $\lambda_{max}$ values of 448 or 648 nm.

q) 4-[(2-bromo-6-nitro-4-trifluoromethylphenyl)azo]-2-octadecyloxy-1-naphthol, mp 90°-92° C. from 2-bromo-6-nitro-4-trifluoromethylaniline (FR-A-2608898), Transmission spectra at an acid or alkaline pH in o-nitrophenyloctyl ether yield $\lambda_{max}$ values of 486 or 600 nm.

r) 4-[(2,5-dichloro-4-nitrophenyl)azo]-2-octadecyloxy-1-naphthol, mp 95° C. from 2,5-dichloro-4-nitroaniline.

u) 4-[(3,5-dinitro-2-thionyl)azo]-2-octadecyloxy-1-naphthol, mp 123°-125° C., from 2-amino-3,5-dinitrothiophene (JP 59-98081) Transmission spectra at an acid or alkaline pH in o-nitrophenyloctyl ether yield $\lambda_{max}$ values of 566 or 624 nm.

v) 4-[(3,5-dicyano-4-methyl-2-thiophenyl)azo]-2-octadecyloxy-1-naphthol, mp 122°-124° C. from 2-amino-3,5-dicyano-4-methylthiophene (DE-A-2359008), Transmission spectra at an acid or alkaline pH in o-nitrophenyloctyl ether yield $\lambda_{max}$ values of 453 or 620 nm.

w) 4-[(5-nitro-2-thiazolyl)azo]-2-octadecyloxy-1-naphthol, mp 105° C. from 2-amino-5-nitro-1,3-thiazole, Transmission spectra at an acid or alkaline pH in o-nitrophenyloctyl ether yield $\lambda_{max}$ values of 459 or 642 nm.

EXAMPLE 4

4-[(2-cyano-4-nitrophenyl)azo]-2-decyloxy-1-naphthol 2-decyloxy-1-naphthol is produced analogously to Examples 2 a) and b) via 2-decyloxynaphthalene. After purification by column chromatography on silica gel 60 (Merck) with ligroin/toluol 2:1 one obtains 32% yellowish oil, $R_f=0.45$.

4-[(2-cyano-4-nitrophenyl)azo]-2-decyloxy-1-naphthol is produced with this using 2-cyano-4-nitroaniline analogous to Example 2 c). After purification of the crude product on silica gel 60 (Merck) with methylene chloride and methylene chloride/methanol 197:3, one obtains 25.6% product as orange-coloured crystals, mp 172°-175° C. Transmission spectra at an acid or alkaline pH in o-nitrophenyloctyl ether yield $\lambda_{max}$ values of 554 or 632 nm.

EXAMPLE 5

The following substances can be produced analogously to Example 4:

a) 4-[(2,6-dibromo-4-nitrophenyl)azo]-2-decyloxy-1-naphthol, mp 93°-95° C. from 2,6-dibromo-4-nitroaniline Transmission spectra at an acid or alkaline pH in o-nitrophenyloctyl ether yield $\lambda_{max}$ values of 454 or 672 nm.

b) 4-[(2-bromo-6-cyano-4-nitrophenyl)azo]-2-decyloxy-1-naphthol, mp 172°-175° C., from 2-bromo-6-cyano-4-nitroaniline, c) 4-[(2,4,6-trinitrophenyl)azo]-2-dexyloxy-1-naphthol, mp 165°-167° C., from 2,4,6-trinitroaniline; Transmission spectra at an acid or alkaline pH in o-nitrophenyloctyl ether yield $\lambda_{max}$ values of 448 or 594 nm.

d) 4-[(3,5-dicyano-4-methyl-2-thiophenyl)azo]-2-decyloxy-1-naphthol, mp 112°-114° C., from 2-amino-3,5-dicyano-4-methylthiophene Transmission spectra at an acid or alkaline pH in o-nitrophenyloctyl ether yield $\lambda_{max}$ values of 458 or 622 nm.

EXAMPLE 6

4-[(2,4-dinitrophenyl)azo]-5-octadecyloxy-1-naphthol a) 5-octadecyloxy-1-naphthol 40 g (0.25 mol) 1,5-dihydroxynaphthalene (Janssen 99%) are suspended in 400 ml freshly distilled dimethylformamide in a 2 l three-neck flask with Claisen attachment, thermometer, calcium chloride tube and dropping funnel and 6 g (0.25 mol) 97% sodium hydride is added in small portions within 40 minutes. In this process the 1,5-dihydroxynaphthalene becomes dissolved with a blue colour and in addition hydrogen is formed and the temperature increases to 36° C. It is stirred for a further 30 minutes and 83.3 g (0.25 mol) 96% 1-octadecyl bromide are added dropwise to the 35° C. warm solution within 10 minutes. Subsequently it is stirred again for 24 hours at room temperature. The crude product which is formed is aspirated vigorously and the residue is stirred with 600 ml water for 15 minutes. This procedure is repeated again and the filter residue is washed so long with water (ca 800 ml) until the filtrate is colourless. Afterwards the filter cake is dried at 40° C. in a drying cupboard over diphosphorus pentoxide. One obtains 98.6 g light beige crystals with a melting point of 76°-78° C.

For the further purification, the product is stirred three times with 750 ml each of ethyl acetate, the undissolved constituents (40.8 g) light beige crystals are filtered off, the mother liquor is treated twice with charcoal and it is concentrated in a vacuum. One obtains 53.2 g (51.9%) beige coloured crystals of the title compound with a melting point of 90°-92° C.

TLC, silica gel 60 (merck), mobile solvent: toluol/methanol=50:1, $R_f=0.36$ b) 4-[(2,4-dinitrophenyl)azo]-5-octadecyloxy-1-naphthol 4-[(2,4-dinitrophenyl)azo]-5-octadecyloxy-1-naphthol is produced with the product from Example 6 a) and 2,4-dinitroaniline analogously to Example 2 c). The purification of the crude product is carried out on silica gel 60 (Merck) with methylene chloride as mobile solvent. The eluate, after recrystallization from toluol/ligroin, yields 30.2% orange-red crystals, Fp 122°-123° C. Transmission spectra at an acid or alkaline pH in o-nitrophenyloctyl ether yield $\lambda_{max}$ values of 470 or 656 nm.

EXAMPLE 7

The following substances can also be produced analogously to Example 6:

a) 4-[(2,6-dibromo-4-nitrophenyl)azo]-5-octadecyloxy-1-naphthol, mp 81°-82° C., from 2,6-dibromo-4-nitroaniline.

b) 4-[(2-chloro-4,6-dinitrophenyl)azo]-5-octadecyloxy-1-naphthol, mp 110°-111° C., from 2-chloro-4,6-dinitroaniline. Transmission spectra at an acid or alkaline pH in o-nitrophenyloctyl ether yield $\lambda_{max}$ values of 445 or 658 nm.

c) 4-[(2-bromo-6-cyano-4-nitrophenyl)azo]-5-octadecyloxy-1-naphthol, TLC, silica gel 60 (Merck), mobile solvent: methylene chloride, $R_f=0.6$, from 2-bromo-6-cyano-4-nitroaniline, Transmission spectra at an acid or alkaline pH in o-nitrophenyloctyl ether yield $\lambda_{max}$ values of 440 or 658 nm.

d) 4[(2-bromo-4-nitrophenyl)azo]-5-octadecyloxy-1-naphthol, TLC, silica gel 60 (Merck), mobile solvent: methylene chloride, $R_f=0.26$ from 2-bromo-4-nitroaniline

EXAMPLE 8

4-[(2,4-dinitrophenyl)azo]-5-decyloxy-1-naphthol a) 5-decyloxy-1-naphthol 12 g (0.3 Mol) sodium hydroxide are dissolved while heating in 500 ml ethanol and a solution of 25 g (0.15 Mol) 1,5-dihydroxynaphthalene 97% is added to the cooled solution within 20 minutes. Afterwards 40.23 g (0.15 Mol) n-decyl iodide is added dropwise within 20 minutes and it is subsequently boiled for 4 hours under reflux. After aspiration of the inorganic residue, the filtrate is concentrated in a vacuum and the dark-brown, semi-crystalline residue is purified by column chromatography on silica gel 60 (Merck). Mobile solvent: toluol/methanol=7:1. After recrystallization from n-heptane the corresponding eluate yields 11.5 g (25.3% of the theroretical yield) product, light-brown crystals, Fp 85°-87° C.

b) 4-[(2.4-dinitrophenyl)azo1-5-decyloxy-1-naphthol

4-[(2,4-dinitrophenyl)azo]-5-decyloxy-1-naphthol is produced analogous to Example 2 c) with the product from Example 8 a) and 2,4-dinitroaniline. The crude product is purified chromatographically on silica gel 60 (Merck). The mobile solvent is methylene chloride. After recrystallization of the appropriate fractions from methylene chloride/ligroin, one obtains 35.6% product as orange-red crystals, Fp 145°-147° C. Transmission spectra at an acid or alkaline pH in o-nitrophenyloctyl ether yield $\lambda_{max}$ values of 448 or 655 nm.

EXAMPLE 9

The following substances can be produced analogously to Example 8:

a) 4-[(2-bromo-4-nitrophenyl)azo]-5-decyloxy-1-naphthol, Fp 83°-87° C. from 2-bromo-4-nitroaniline Transmission spectra at an acid or alkaline pH in o-nitrophenyloctyl ether yield $\lambda_{max}$ values of 445 or 672 nm.

b) 4-[(2-chloro-4-nitrophenyl)azo]-5-decyloxy-1-naphthol, Fp 94°-97° C., from 2-chloro-4-nitroaniline, Transmission spectra at an acid or alkaline pH in o-nitrophenyloctyl ether yield $\lambda_{max}$ values of 444 or 674 nm.

c) 4-[(2-chloro-4,6-dinitrophenyl)azo]-5-decyloxy-1-naphthol, Fp 134°-135° C., from 2-chloro-4,6-dinitroaniline, Transmission spectra at an acid or alkaline pH in o-nitrophenyloctyl ether yield $\lambda_{max}$ values of 436 or 656 nm.

d) 4-[(2-bromo-6-cyano-4-nitrophenyl)azo]-5-decyloxy-1-naphthol, Fp 110°-114° C., from 2-bromo-6-cyano-4-nitroaniline, Transmission spectra at an acid or alkaline pH in o-nitrophenyloctyl ether yield max values of 446 or 658 nm.

EXAMPLE 10

General instructions for the production of test carriers

For the production of a test carrier according to FIG. 1, transparent polyester foil (200 μm thick) is coated with the mixtures mentioned in the following Examples and dried. The coated foil is cut into 15 mm wide strips and glued as layer (1) with hot-melting adhesive longitudinally onto 150 mm wide white polyester foil (5). Strips of glass fibre fleece with a basis weight of 30 g/m² as transport layer (2), of glass fibre fleece with an area weight of 60 g/m² as separation layer (3) and of polyamide fabric as protective layer (4) are also glued longitudinally onto this white polyester foil so that after cross-cutting 6 mm wide test strips according to FIG. 1 are formed.

Test carriers according to FIG. 2 are produced analogously. The layer (11) consists of filter paper which is impregnated with a buffer substance.

The film layer or test carrier according to the present invention are used in such a way that 30 μl of the sample to be examined is applied to the polyamide fabric (4) and the test carrier is then inserted into the commercial reflectance photometer Reflotron ® (Boehringer Mannheim GmbH, Mannheim, Federal Republic of Germany). The liquid penetrates into the glass fibre pad (3), where in the case of whole blood the erythrocytes are separated, and reaches the glass fibre zone (2) which serves as the transport layer. In the reflectance photometer the film under the flap (1) or (10) is brought into contact with the liquid in the transport layer (2) by pressure on the flap and the colour formed is measured by reflectance photometry at 642 nm and 37° C.

EXAMPLE 11

A mixture of the following composition is produced and applied with a wet film thickness of 300 μm to a transparent polyester foil and dried:

| | |
|---|---|
| Vinylacetate-vinyllaurate-copolymer (Vinnapas ® B 500/20 VL, Wacker Chemie, Munich, Germany) | 11.8 g |
| 2,2-diphenyl-1-cyano-acrylic acid-ethyl-hexylester (Uvinul ® N539, BASF, Ludwigshafen, Germany) | 14.4 g |
| 4-[(2-chloro-4-nitrophenyl)azo-]-5-decyloxy-1-naphthol (from Example 9 b) | 0.0573 g |
| Valinomycin | 0.2406 g |
| Diatomaceous earth (Celatom ® MW 25, Eagle-Picher, Cincinatti, USA) | 22.6 g |
| Butyl acetate | 40.7 g |

A second layer of the following composition having a wet film thickness of 150 μm is applied to this layer and dried in the same way.

| | |
|---|---|
| Hydroxyethyl cellulose (Natrosol ® 250 G, Hercules Inc., Willmington, Delaware, USA) 2% in water | 25 g |
| Citric acid | 2.18 g |
| Ethanol | 35 ml |
| adjusted to pH 5.0 with LiOH. | |

Test strips are produced from the coated foil as described in Example 10 and measured. The measurement takes place 60 seconds after contact of the sample with the reagent film.

When sera are used with different contents of potassium the following dependence of the reflectance (%R) on the potassium content is found:

TABLE 2

| Potassium content [mmol potassium/l] | Reflectance [% R] |
|---|---|
| 0.24 | 49.5 |
| 1.09 | 45.5 |
| 1.87 | 43.3 |
| 3.18 | 39.7 |
| 4.15 | 38.8 |
| 6.08 | 34.6 |

TABLE 2-continued

| Potassium content [mmol potassium/l] | Reflectance [% R] |
| --- | --- |
| 8.10 | 32.3 |
| 10.22 | 31.3 |
| 12.10 | 29.7 |

Similar results are obtained With the following naphthol derivatives according to the present invention:
a) 4-[(2-chloro-4,6-dinitrophenyl)azo]-5-octadecyloxy-1-naphthol, (Example 7 b).
b) 4-[(2-chloro-4,6-dinitrophenyl)azo]-2-octadecyloxy-1-naphthol, (Example 3 i).

EXAMPLE 12

A test strip is produced in analogy to Example 11 except that 0.0779 g 4-[(2,6-dibromo-4-nitrophenyl)azo-]-2-octadecyloxy-1-naphthol (Example 2) is used as the pH indicator and 2.67 g N,N-bis-(hydroxyethyl)-aminoethanesulfonic acid (BES) adjusted to pH 7.0 with LiOH is used as the buffer.

The values measured with sera having different contents of potassium are as follows:

TABLE 3

| Potassium content [mmol potassium/l] | Reflectance [% R] |
| --- | --- |
| 0.24 | 51.6 |
| 1.09 | 46.2 |
| 1.87 | 42.8 |
| 3.18 | 38.6 |
| 4.15 | 36.5 |
| 6.08 | 33.1 |
| 8.10 | 30.4 |
| 10.22 | 28.5 |
| 12.10 | 27.0 |

Similar results are obtained with the following pH indicators:
a) 4-[(2-cyano-4-nitrophenyl)azo]-2-octadecyloxy-1-naphthol (Example 3 f),
b) 4-[(2-cyano-4-nitrophenyl)azo-]-2-decyloxy-1-naphthol (Example 4),
c) 2-(3,7,11,15-tetramethyl-2-hexadecenyl)-3-methyl-4-[(2,4-dinitrophenyl)azo]-1-naphthol (Example 1 a),
d) 4-[(2-bromo-4-nitro-6-trifluoromethyl-phenyl)azo-]-2-octadecyloxy-1-naphthol (Example 3 p).

EXAMPLE 13

A test strip is produced in analogy to Example 11 except that 0.0634 g 2-(3,7,11,15-tetramethyl-2-hexadecenyl)-3-methyl-4-[(4-nitrophenyl)-azo]-1-naphthol (Example 1 b) is used as the indicator and 0.773 g boric acid adjusted to pH 9.5 with LiOH is used as the buffer.

Using sera with different contents of potassium the following reflectance values are measured:

TABLE 4

| Potassium content [mmol potassium/l] | Reflectance [% R] |
| --- | --- |
| 0.24 | 52.7 |
| 1.09 | 47.3 |
| 1.87 | 43.6 |
| 3.18 | 39.3 |
| 4.15 | 37.7 |
| 6.08 | 33.9 |
| 8.10 | 31.4 |
| 10.22 | 29.4 |
| 12.10 | 27.9 |

Similar results are obtained with the following indicators:
a) 4-[(2-bromo-4-nitrophenyl)azo-]-5-decyloxy-1-naphthol (Example 9 a),
b) 2-(3,7,11,15-tetramethyl-2-hexadecenyl)-3-methyl-4-[(2,4-dinitrophenyl)azo]-1-naphthol (Example 1 a),
c) 2-(3,7,11,15-tetramethyl-2-hexadecenyl)-3-methyl-4-[(2-methyl-4-nitrophenyl)azo]-1-naphthol (Example 1 c),
d) 2-(3,7,11,15-tetramethyl-2-hexadecenyl)-3-methyl-4-[(5-nitro-2-thiazolyl)azo]-1-naphthol (Example 1 j).

We claim:
1. Compound of the formula

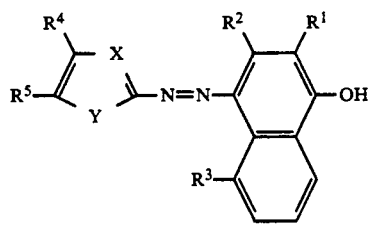

wherein
$R^1$, $R^2$ and $R^3$ are the same or different and are selected from the group consisting of hydrogen, an alkyl group and an alkoxy group, with the proviso that at least one of $R^1$, $R^2$ and $R^3$ is $C_8-C_{30}$ alkyl group or a $C_8-C_{30}$ alkoxy group;
$R^4$ is hydrogen or an alkyl group
$R^5$ is a nitro group, an alkyl group substituted by halogen, a cyano group, a sulfonamido group or an alkylsulfonyl group;
X is nitrogen or $CR^6$,
Y is sulphur or $CR^7=CR^8$,
wherein $R^6$, $R^7$ and $R^8$ are the same or different and are selected from the group consisting of hydrogen, halogen, a nitro group, a cyano group, an alkyl group, a halogen substituted alkyl group and an alkylsulphonyl group.

2. Compound of claim I, wherein two of $R^1$, $R^2$ and $R^3$ are hydrogen, or a $C_1-C_4$ alkyl group.

3. Compound of claim 1, wherein $R^1$ is a $C_{10}-C_{20}$ alkoxy group, and both $R^2$ and $R^3$ are hydrogen.

4. Compound of claim 1, designated 4-[2-chloro-4-nitro-phenyl)azo-]-5-decyloxy-1-naphthol.

5. Compound of claim 1, designated 4-[(2,6-dibromo-4-nitro-phenyl)azo-]-2-octadecyloxy-1-naphthol.

6. Compound of claim 1, designated 4-[(2-cyano-4-nitro-phenyl)azo]-2-octadecyloxy-1-naphthol.

7. Compound of claim 1, designated 4-[(2-cyano-4-nitro-phenyl)azo-]-2-decyloxy-1-naphthol.

8. Compound of claim 1, designated 2-(3,7,11,15-tetramethyl-2-hexadecenyl)-3-methyl-4-[(2,4-dinitrophenyl)azo]-1-naphthol.

9. Compound of claim 1, designated 4-[(2-bromo-4-nitro-6-trifluoromethyl-phenyl)azo-]-2-octadecyloxy-1-naphthol.

10. Compound of claim 1, designated 2-(3,7,11,15-tetramethyl-2-hexadecenyl) -3-methyl-4-[(4-nitrophenyl)-azo]-1-naphthol.

11. Compound of claim 1, designated 4-[(2-bromo-4-nitro-phenyl)azo-]-5-decyloxy-1-naphthol.

12. Compound of claim 1, designated 2-(3,7,11,15-tetramethyl-2-hexadecenyl) -3-methyl-4-[(2-methyl-4-nitrophenyl)azo]-1-naphthol.

13. Compound of claim 1, designated 2-(3,7,11,15-tetramethyl-2-hexadecenyl) -3-methyl-4-[(5-nitro-2-thiazolyl)azo]-1-naphthol.

14. The compound of claim 1 designated 4-[(2-chloro-4,6-dinitrophenyl)azo]-5-octadecyloxy-1-naphthol.

15. Compound of claim 1, designated 4-[(2-chloro-4,6-dinitrophenyl)azo]-2-octadecyloxy-1-naphthol.

16. Composition useful in determining an ion in an aqueous liquid comprising an ionophore and a compound of claim 1 in a water immiscible medium.

17. Composition of claim 16, wherein said ionophore is valinomycin.

18. Composition of claim 16, further comprising a buffer.

19. Method for determination of pH of a liquid sample, comprising contacting said liquid sample with a compound of claim 1 and determining formation of a color or a color change as an indication of pH of said liquid.

20. Method for determining an ion in an aqueous sample comprising contacting said liquid sample with a water immiscible composition comprising:
   (a) an ionophore, and
   (b) a naphthol derivative compound designated

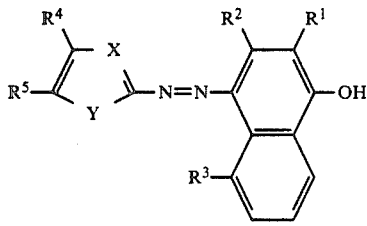

wherein $R^1$, $R^2$ and $R^3$ are the same or different and are selected from the group consisting of hydrogen, an alkyl group and an alkoxy group, with the proviso that at least one of $R^1$, $R^2$ and $R^3$ is a $C_8$–$C_{30}$ alkyl group or a $C_8$–$C_{30}$ alkoxy group;

$R^4$ is hydrogen or an alkyl group;

$R^5$ is a nitro group, an alkyl group substituted by halogen, a cyano group, a sulfonamido group or an alkylsulfonyl group;

X is nitrogen or $CR^6$,

Y is sulphur or $CR^7=CR^8$, wherein $R^6$, $R^7$ and $R^8$ are the same or different and are selected from the group consisting of hydrogen, halogen, a nitro group, a cyano group, an alkyl group, a halogen substituted alkyl group and an alkylsulphonyl group, under conditions favoring complexing of said ion with said ionophore and causing release of a hydrogen ion from said compound to form a color or a color change, and determining said color or color change as a determination of said ion.

21. Method of claim 20, wherein said ion is potassium.

22. Method of claim 20, wherein said ionophore is valinomycin.

23. Method of claim 20 wherein in said naphthol derivative compound two of $R^1$, $R^2$ and $R^3$ are hydrogen or a $C_1$–$C_4$ alkyl group.

24. Method of claim 20 wherein in said naphthol derivative compound $R^1$ is a $C_{10}$–$C_{20}$ alkoxy group and both $R^2$ and $R^3$ are hydrogen.

25. Method of claim 20 wherein said naphthol derivative compound is 4-[2,6-dibromo-4-nitrophenyl)azo]-2-octadecyloxy-1-naphthol.

26. Method of claim 20 wherein said naphthol derivative compound is 4-[(2-bromo-4-nitro-6-trifluoromethylphenyl)azo]-2-octadecyloxy-1-naphthol.

* * * * *